(12) United States Patent
Lee et al.

(10) Patent No.: US 7,550,734 B1
(45) Date of Patent: Jun. 23, 2009

(54) INTEGRATED HETERODYNE TERAHERTZ TRANSCEIVER

(75) Inventors: Mark Lee, Albuquerque, NM (US); Michael C. Wanke, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 93 days.

(21) Appl. No.: 11/698,010

(22) Filed: Jan. 25, 2007

Related U.S. Application Data (60) Provisional application No. 60/761,871, filed on Jan. 25, 2006.

(51) Int. Cl.
*G01T 1/24* (2006.01)

(52) U.S. Cl. .................................. 250/370.12

(58) Field of Classification Search ............ 250/370.12, 250/341.8; 257/E31.066; 702/75; 455/189.1
See application file for complete search history.

(56) References Cited

U.S. PATENT DOCUMENTS

| | | | |
|---|---|---|---|
| 7,376,403 B1 * | 5/2008 | Wanke et al. ............ | 455/189.1 |
| 2002/0036814 A1 * | 3/2002 | Mueller et al. ............. | 359/180 |
| 2006/0167641 A1 * | 7/2006 | Chamberlin et al. ......... | 702/75 |

OTHER PUBLICATIONS

H.-W. Hubers et al, "Terahertz quantum cascade laser as local oscillator in a heterodyne receiver", Optics Express, vol. 13, No. 15, Jul. 25, 2005, pp. 5890-5896.

Qing Hu et al, "Resonant-phonon-assisted THz quantum-cascade lasers with metal-metal waveguides", Semiconductor Science and Technology, 2005, vol. 20, pp. S228-S236.

J.R. Gao et al, "Terahertz heterodyne receiver based on a quantum cascade laser and a superconducting bolometer," Applied Physics Letters, 2005, vol. 86 pp. 244104-1 through 244104-3.

Stephen Kohen, et al "Electromagnetic modeling of terahertz quantum cascade laser waveguides and resonators," Journal of Applied Physics, vol. 97, 2005, pp. 053106-1 through 053106-9.

R. Sachs et al, "Mode calculations for a terahertz quantum cascade laser," Optics Express, vol. 12, No. 10, May 17, 2004, pp. 2062-2069.

Olivier Demichel et al, "Surface Plasmon photonic structures in terahertz quantum cascade lasers," Optics Express, vol. 14, No. 12, Jun. 12, 2006, pp. 5335-5345.

Rudeger Kohler et al, "Terahertz semiconductor-heterostructure laser," Nature, vol. 417, May 9, 2002, pp. 156-159.

* cited by examiner

*Primary Examiner*—David P Porta
*Assistant Examiner*—Faye Boosalis
(74) *Attorney, Agent, or Firm*—Kevin W. Bieg (57) ABSTRACT

A heterodyne terahertz transceiver comprises a quantum cascade laser that is integrated on-chip with a Schottky diode mixer. An antenna connected to the Schottky diode receives a terahertz signal. The quantum cascade laser couples terahertz local oscillator power to the Schottky diode to mix with the received terahertz signal to provide an intermediate frequency output signal. The fully integrated transceiver optimizes power efficiency, sensitivity, compactness, and reliability. The transceiver can be used in compact, fieldable systems covering a wide variety of deployable applications not possible with existing technology.

15 Claims, 4 Drawing Sheets

INTEGRATED HETERODYNE TERAHERTZ TRANSCEIVER

CROSS-REFERENCE TO RELATED APPLICATION

This application claims the benefit of U.S. Provisional Application No. 60/761,871, filed Jan. 25, 2006, which is incorporated herein by reference.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to terahertz radiation technology and, in particular, to a microelectronics-based integrated heterodyne terahertz transceiver.

BACKGROUND OF THE INVENTION

Terahertz (THz) technologies utilize electromagnetic radiation generally in the frequency range between 100 GHz and 10 THz (i.e., wavelengths of 3 mm to 30 μm, energies of 0.4 to 40 meV, or equivalent blackbody radiation temperatures of 5 K to 500 K). Terahertz technologies have many potential applications in diverse fields, including space and atmospheric sciences, molecular spectroscopy, remote sensing, biology, medical imaging, and communications.

Historically, there has been much interest in terahertz technologies for high-resolution spectroscopy for space, planetary, and Earth science. For example, much of the interstellar medium radiates in the terahertz region, somewhat above the cosmic microwave background, enabling terahertz measurements to probe star formation and the early universe. Planetary atmospheres have background temperatures of tens to several hundred degrees Kelvin, enabling terahertz observation of extraterrestrial atmospheric conditions. Furthermore, thermal emission lines in the terahertz region from gases in the Earth's stratosphere and upper troposphere provide important indicators of ozone destruction, global warming, and pollution.

Metals and polar liquids, such as water, are opaque in the terahertz region. However, many non-metallic materials that are visually opaque are partially transparent or exhibit molecular resonances in the terahertz region. For example, many solids, notably oxides and organic solids, have distinct series of optically-active lattice vibration modes that cause large optical absorption resonances in the range 1 to 10 THZ. While such lattice vibration resonances are relatively broad, if the "signatures" are known they can be used to identify the solid.

In the gas phase, molecular spectral signatures can be used to detect and identify molecules with high speed, sensitivity, and very high specificity. Many molecules, from simple diatomic chemicals to complex macromolecules, have stronger and more distinctive absorption and emission resonances in the terahertz region than in either microwave or near infrared-to-visible ranges. Especially at lower pressures, smaller molecules generally have very sharp terahertz signatures, with Doppler limited widths around 1 MHz, providing significantly enhanced spectral resolution as compared to infrared signatures. Nearly all non-centrosymmetric molecules have resonances between 0.1 to 10 THz that are predominately rotational modes or hybrid rotational-vibrational modes, determined by a molecule's moment-of-inertia. Since the moment-of-inertia depends on the distribution of mass within the molecule as well as total mass, a spectrum based on moment-of-inertia can discriminate between molecular species better than spectroscopy based only on mass. Compared to microwave spectroscopy, interaction strengths are generally larger in the terahertz region since the strength of the interaction increases by greater than the square of the frequency, until reaching a peak in the terahertz region that is specified by the molecular mass. Such high molecular absorption/emission cross-sections can provide potentially excellent signal-to-noise detection levels and thus high sensitivity to trace concentrations of molecules. Further, at high spectral resolution each molecular signature is unique enough that only a few lines are generally needed to identify a molecule. Therefore, rotational absorption spectroscopy can be used to unambiguously identify molecules in the gas phase, even in the presence of contaminants, whereas vibrational spectroscopy lacks such molecular specificity. Further, for gas molecules that are at a higher temperature than the background, the characteristic spectral emission features will be observable passively as well as actively. Therefore, the terahertz region has enormous potential in the area of remote spectroscopy with unprecedented, unsurpassed species discrimination capability and minimized probability of error due to either missed detection or misidentification.

Biological identification using optical techniques typically uses either standoff detection, using some specific spectroscopic signature, for example, native fluorescence upon UV excitation or infrared-absorption/Raman signatures, or contact techniques, wherein the target biomolecule is made to react with other chemical compounds or biomolecules, and further fluorescent tagging makes the detection possible. An example of this later method is the sandwich immunoassay for protein detection. For both methods, the terahertz region of the electromagnetic spectrum is attractive for label-free detection of biomolecules, since there is a very high density of vibrational-rotational modes that can be accessed through direct absorption or other dielectric coefficient sensing techniques.

For example, the vibrational spectrum at low frequencies in the range of 0.1-3 THz is particularly sensitive to structural changes of proteins, such as conformational changes that occur upon protein capture by antibodies and other hybridization reactions. As a result, guided-wave terahertz biosensors can be used effectively for label-free biosensing. Examples of established optical techniques for label-free biosensing are surface plasmon resonance (SPR), surface acoustic wave (SAW) detection. These techniques usually rely on measuring the change of a material property caused by a protein-ligand interaction with great sensitivity. In SPR, the adsorbed layers cause a change in refractive index whereas in SAW (or quartz crystal monitoring) detection it is a pure mass loading change. Conversely, a terahertz biosensor can be sensitive to the conformational changes that occur upon protein-ligand binding.

A highly desirable application of terahertz technology is to do imaging of objects at useful standoff distances in real time for object or pattern recognition. Since terahertz waves have a much smaller wavelength than microwaves, they can provide sub-millimeter spatial resolution. Because terahertz irradiation does not involve the health and safety issues of ionizing radiation, such as are a concern with X-ray imaging, applications of terahertz technologies may include noninvasive tomographic imaging or spectroscopic characterization of biological materials. A primary advantage of terahertz imaging for security applications is that many materials that are completely opaque or highly reflective at microwave and/or infrared-visible frequencies are at least partially transparent in the terahertz. Therefore, because terahertz radiation is nondestructive and can penetrate non-metallic and non-polarizing external coverings (e.g., clothing, paper, wood, and plastics), the technology may be useful in security screening for hidden explosives and concealed weapons. Terahertz technologies can be used to either detect or preferably image something otherwise hidden behind such a covering material, using either active or passive methods. Finally, terahertz imaging may also be useful for industrial processes, such as package inspection and quality control.

Finally, terahertz signals can have a high bandwidth and are potentially useful for free-space communications. Therefore, terahertz technologies may be useful for space-based communications, such as satellite-to-satellite. However, limited atmospheric propagation, due to water and oxygen absorption, has discouraged the development of terahertz technologies for radar and terrestrial communications. Nonetheless, the technology may be attractive for relatively secure short-range communications, such as wireless communications in situations in which short-burst beamed messages with limited broadcast range is desirable. A terahertz carrier has a higher frequency than microwaves, enabling higher data rates (e.g., about 10 GB/sec). Further, the shorter wavelength enables higher directionality.

However, beyond basic science, these applications in the terahertz region are relatively undeveloped. Much progress is still required to provide field-deployable terahertz systems, especially for military, anti-terror, and biomedical imaging applications. Terahertz applications remain relatively undeveloped because the terahertz region lies between the traditional microwave and optical regions of the electromagnetic spectrum, where electronic or photonic technologies have been developed for these purposes. Terahertz applications have been hampered due to the historically poor performance of terahertz components lying in the "technological gap" between these traditional electronic and photonic domains. Furthermore, atmospheric opacity is strong in the terahertz, so that terahertz components must meet extremely stringent signal-to-noise requirements for any in-atmosphere stand-off application, unfortunately also in a frequency range where conventional technologies have inadequate performance.

In particular, the generation and detection of electromagnetic fields at terahertz frequencies has been difficult. To date, active terahertz generators have only demonstrated relatively low power capability. Traditional electronic solid state sources based on semiconductors are limited by electron transit times and roll-off at severely high frequencies (i.e., limited to less than about 0.1 THz). Tube sources are difficult to scale to small sizes, due to the extremely high fields and current densities required. Traditional semiconductor diode lasers are limited by normal optical bandgaps to frequencies greater than about 25 THz. Therefore, frequency conversion techniques have typically been used to reach terahertz frequencies, including upconversion of millimeter waves using electronic or multiple harmonic techniques, or downconversion from the visible or near-infrared using frequency mixing/switching or nonlinear optical processes. However, continuous microelectronic sources using either microwave upconverters or infrared downconverters have difficulty exceeding 1 µW average power at around 2 to 3 THz.

Semiconductor lasers are inherently compact and durable, due to their internal, electrically-pumped optical cavity and low power requirement. Recently, terahertz sources based on quantum cascade lasers (QCLS) have produced relatively high power in a compact size. QCLs are the first semiconductor sources of terahertz radiation capable of average powers in a pulsed mode in excess of 250 mW at cryogenic temperatures. QCLs are unipolar semiconductor devices comprising complex layered heterostructures of two or more semiconductor alloys forming an active waveguide core, typically mounted on a metallic heat-sink. The complex QCL structure can be grown by molecular beam epitaxy (MBE). MBE enables accurate control of the sub-nanometer semiconductor layers with high reproducibility over hundreds of periodic layers.

Quantum cascade lasers rely on the emission from transitions between subbands in a quantum well. Light is produced in an active region by intersubband transitions of a single charge carrier (i.e., an electron) between two quantized levels in the conduction band. In a QCL biased at an operating voltage, a photon is emitted by an intrawell transition between an upper level and a lower level in an active region. To achieve population inversion for lasing, electrons must be injected rapidly into the upper level and then rapidly extracted from the lower level and tunnel into the upper level of the downstream active region. To maximize the gain, tens to hundreds of these active regions can be cascaded together, enabling electrons that are recycled from one active region to the next to emit more than one photon per pass through the device, enabling high emission power. Because the energy difference between the two quantized levels is determined by the specific structure design (i.e., the quantum well and barrier widths), the laser can be band-structure engineered to emit at any wavelength within a broad spectral range. To minimize device loses and confine the terahertz radiation to the gain material, the active region can be inserted into a waveguide. Laser action requires that the gain be adequate to overcome device losses, primarily due to free-carrier losses in the waveguide and mirror losses. Many variations on this basic scheme have evolved.

However, the weak radiation output from passive and traditional active terahertz sources, the low photon energies of terahertz radiation, and high atmospheric attenuation due to molecular absorption (e.g., water vapor) frequently results in a weak received terahertz signal that may be difficult to distinguish from noise. Therefore, terahertz detection can also be difficult. Current terahertz detectors include both direct and heterodyne detectors.

Direct detectors generally directly convert the received power to a voltage or current that is proportional to the incoming power. Examples of direct detectors include rectifiers, bolometers, and pyroelectrics. A common direct detector uses antenna coupling to a small area Schottky diode that responds directly to the terahertz electric field. Detection depends on the nonlinear rectification properties of a metal-semiconductor junction. Advantages of the Schottky diode include a useful sensitivity over a large wavelength range, large instantaneous bandwidth, excellent performance at room temperature, and ease of fabrication.

For shorter wavelengths (i.e., frequencies above 1 THz), direct detectors generally have good responsivity and are sensitive to a broad band of frequencies. However, direct detectors generally provide no frequency discrimination, unless they are coupled with an external resonator or interferometer. Furthermore, they are sensitive to incoherent background noise and interference. Finally, direct directors are typically very slow, with 1 to 10 ms response times required to obtain an adequate signal-to-noise. Therefore, direct detectors have been used mainly for wideband applications, such as thermal imaging.

Heterodyned detection is desirable for some terahertz applications. Especially at low pressures such as a space environment, terahertz signatures of many molecules are very unique, enabling identification even with only a few spectral lines over a narrow spectral region. However, because the emission lines can be quite narrow and may be closely spaced, high resolution spectroscopy is desirable to take full advantage of terahertz discrimination capabilities. High-resolution heterodyne detection covering the frequency intervals of expected signatures is highly desirable for these applications. Further, particularly for weak signals, heterodyning can be used to coherently downconvert the terahertz signal to increase signal-to-noise by reducing bandwidth. The downconverted signal can then be post-amplified and processed using conventional microwave techniques.

Heterodyne mixers beat the signal RF frequency against a known local oscillator (LO) frequency to generate an intermediate frequency (IF) difference signal that is tunable through the LO frequency. The LO can have a fixed output power that is generally much greater than the power of the received RF signal. A nonlinear mixer produces an IF output power that is proportional to the product of the powers of the received RF signal and the LO signal. Mixers display good rejection of incoherent noise and interference. They are typically fast, with IF bandwidths of 0.1 to 10 GHz. Furthermore, narrowband detectors do not require additional frequency selective elements to analyze the spectrum of the incoming terahertz radiation as long as the received RF signal is within an IF bandwidth of the LO frequency. Therefore, heterodyne detectors have been used in narrow frequency band, high-resolution applications at lower terahertz frequencies, such as for molecular spectroscopy. Common mixers are field-type devices that have a strong quadratic nonlinearity.

However, a fast solid-state terahertz radiation mixer is still needed to enable coherent detection for terahertz applications requiring high resolution. In particular, a microelectronic-based integrated heterodyne terahertz transceiver is highly desirable for field-deployable applications. Such a transceiver requires the successful integration of both terahertz detectors and sources on a single chip, along with cooling, optics and control electronics, while maintaining high source power (e.g., greater than 10 mW), detection sensitivity, and operating temperatures, all in a compact, reliable, integrated package.

SUMMARY OF THE INVENTION

The present invention is directed to an integrated heterodyne terahertz transceiver comprising a quantum cascade laser, comprising a substrate providing a bottom waveguide layer, a plurality of layered heterostructures of two or more semiconductor alloys on the substrate, a top waveguide layer on the layered semiconductor heterostructures, thereby providing an active semiconductor core between the top and bottom waveguide layers; and at least one receiver formed in a hole in the top waveguide layer of the quantum cascade laser, comprising a rectifying metal contact on the top surface of the layered semiconductor heterostructures exposed by the hole, thereby forming a metal-to-semiconductor Schottky diode, and an antenna or horn connected to the rectifying metal contact for receiving a terahertz signal; wherein the quantum cascade laser couples terahertz local oscillator power to the Schottky diode to mix with the received terahertz signal to provide a intermediate frequency output signal. The fully integrated transceiver optimizes power efficiency, sensitivity, compactness, and reliability. The transceiver can be used in compact, fieldable systems covering a wide variety of deployable applications not possible with existing technology.

For example, the transceiver can be used for high-specificity, real-time point detection. Especially at low pressures, terahertz signatures of many molecules are very unique, enabling identification even with only a few spectral lines over a narrow spectral region. Thus in accessible areas, compact point sensors based on terahertz signatures can be very specific tools for identifying many important compounds. These point sensors can form a sniffer system used to monitor emissions from facilities to portals to look for materials, such as explosives. The narrow linewidth of the local oscillator combined with the resolution of the heterodyne mixer yields very high specificity in this type of application.

The transceiver can also be used for high-specificity, real time, passive detection. With existing terahertz components integrated into a heterodyne transceiver, passive remote detection is possible from radiative emission of gases hot with respect to the background or absorption by gases backlit by hotter backgrounds. This enables, for example, identifying effluent emissions from exhaust stacks, and byproducts of explosions or fuel combustion. Without heterodyne detection the thermal background would prevent success in these types of environments.

The transceiver can also be used for high-specificity, real time, active detection. Active remote sensing can be utilized, for example, via differential absorption laser spectroscopy (DIAL). With DIAL, temperature differences are not required for detection and range is limited by source power and backscatter cross-section. This can be used for short-range portal applications, looking through materials such as clothing or packaging materials for reflection as well as emission spectra, to mid-range applications of discriminating chemical and biological agents in a cloud, to multi-km range exoatmospheric radar type applications. The heterodyne/homodyne nature of the detection using a transceiver is essential for these applications by increasing signal-to-noise of the measurement by orders of magnitude compared to direct detectors combined with a separate laser source.

The transceiver can be used as a high-resolution spectroscopy tool for enhanced signature development. The transceiver enables higher resolution spectroscopy over a differential frequency range determined by the bandwidth of the mixer detector centered on a sharply defined terahertz laser frequency. Terahertz QCLs have narrower linewidths than the Doppler-limited linewidth of 1 MHz (in the THz), which is significantly better resolution than Fourier-Transform Infrared (FTIR) methods (about 60 MHz). Especially for heavier molecules, this QCL-limited linewidth enables cataloguing features otherwise unobservable with FTIR spectroscopy, which is critical for accurate modeling and assignment of remotely measured signatures.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

FIG. 4B shows a top-view schematic illustration of the transceiver. In this embodiment, a small hole (or array of holes) can be fabricated through the QCL's top electrical contact metallization to expose the underlying semiconductor. A mixer (or array of mixers) is fabricated or flip-chipped into these holes to form a metal-to-semiconductor Schottky diode mixer. The mixer protrudes into the propagating terahertz field inside the QCL ridge cavity, so that a small fraction of the internal terahertz field is drawn off to supply LO power to the mixer. The transceiver's target illumination signal can be broadcast from an end facet of the QCL. The return signal from the target is received by an antenna connected to the metal anode of the mixer diode. Alternatively, if the target passively emits its own terahertz radiation, emission from the end facet can be blocked and the device can operate purely as a heterodyne receiver.

DETAILED DESCRIPTION OF THE INVENTION

Figure 1:
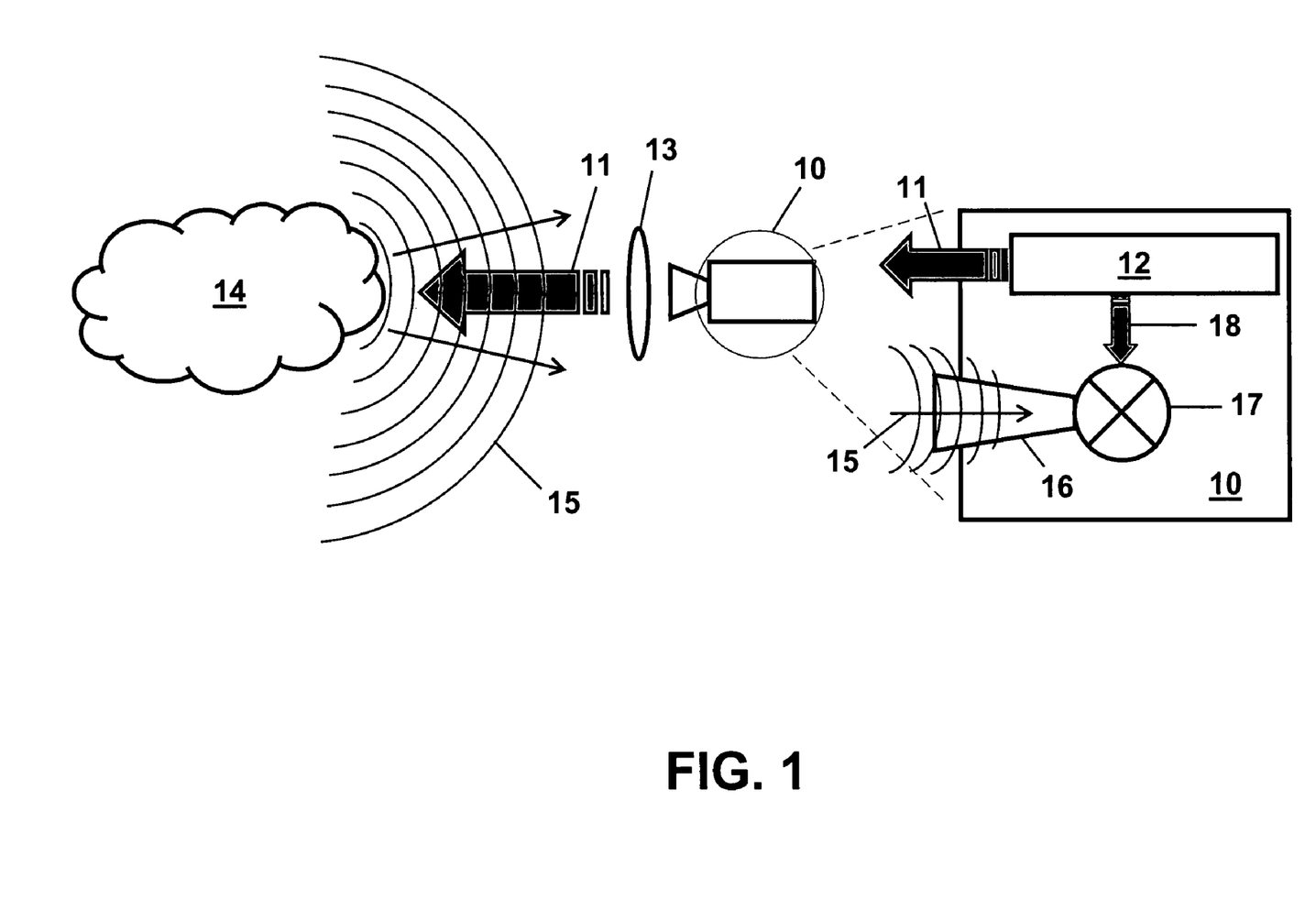
FIG. 1 shows a schematic illustration of an active remote sensing system comprising an integrated heterodyne terahertz transceiver. In such a remote sensing system, the transceiver provides a terahertz source that illuminates a target at a known frequency. The return terahertz signal radiating from the target is collected by optics and detected by a heterodyne mixer on the transceiver. The terahertz source, in addition to illuminating the target, also acts as the LO for the mixer detector to define a detection frequency reference. The mixer detects terahertz radiation within a limited bandwidth around the LO frequency and is insensitive to signals at frequencies outside this bandwidth, thereby rejecting noise outside the detection bandwidth.

In FIG. 1 is shown a schematic illustration of an active remote sensing system comprising a heterodyne terahertz transceiver 10 that integrates a terahertz transmitter with a terahertz receiver. The transceiver 10 transmits terahertz radiation 11 from a QCL source 12 at a known frequency. The terahertz radiation 11 can be collimated by optics 13 to illuminate a remote object, or target 14. A return terahertz signal 15 is radiated from the target 14 and is collected by the optics 13 and detected by the transceiver 10. The returned signal 15 is received by a horn or antenna 16 and coupled to a mixer 17 of the transceiver 10. The mixer 17 can comprise a Schottky-type diode (for heterodyning, the Schottky diode is referred to herein as a mixer). A portion of the transmit power is coupled from the QCL 12 to the mixer 17 as a LO 18 to define a detection frequency reference. An IF circuit (not shown) processes the mixer output. The mixer 17 therefore detects terahertz radiation within a limited bandwidth around the LO frequency and is insensitive to signals at frequencies outside this bandwidth, thereby rejecting noise outside the detection bandwidth.

Figure 2:
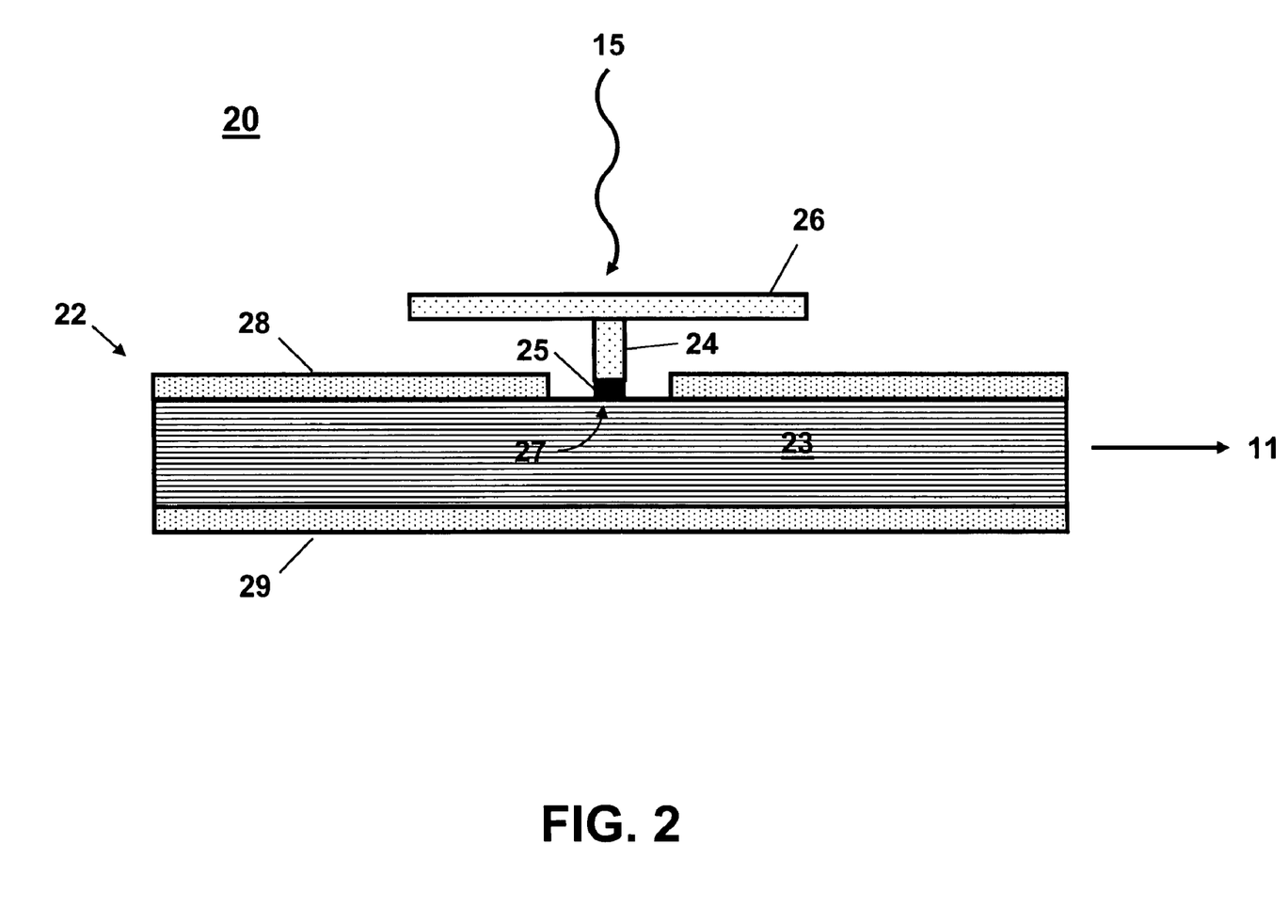
FIG. 2 shows a schematic illustration of an integrated heterodyne terahertz transceiver. The terahertz source portion of the transceiver comprises of a terahertz QCL structure. The terahertz heterodyne mixer portion of the transceiver comprises a Schottky-type diode (i.e., metal-to-semiconductor contact diode) that is directly integrated with the QCL structure and draws its LO frequency reference from the internal electromagnetic field in the QCL structure.

In FIG. 2 is shown a schematic illustration of an exemplary embodiment 20 of the integrated heterodyne terahertz transceiver 10. The transceiver 20 integrates onto a single semiconductor chip platform a terahertz QCL 22 and a single or a linear array of Schottky diode mixers 27. The QCL 22 supplies the LO source for the mixer 27 and also, if needed, a coherent active illumination source 11. When the QCL 22 is used as an active illumination source, the mixer 27 can phase lock onto the LO, yielding extremely high rejection of background interference.

The QCL 22 comprises a plurality of layered heterostructures of two or more semiconductor alloys forming an active semiconductor core 23 between a top waveguide layer 28 and a bottom waveguide layer 29. The design of the heterostructure can vary, depending on the transceiver requirements. Typically, the active region in the heterostructure is repeated many times until the stack thickness is about ten microns, although thicker or thinner stacks can also be used. For example, in Table 1 is shown the heterostructure for a QCL designed to operate at 2.92 THz (i.e., wavelength of 103 μm) when biased at 9.87 kV/cm. The heterostructure can be built up by MBE on a semi-insulating (SI) gallium arsenide substrate. The heterostructure comprises alternating thin layers of GaAs and AlGaAs. The active region in this example is repeated 178 times. Such GaAs/AlGaAs heterostructures can typically operate in a range of about 2.0 to 4.5 THz. However, other heterostructure designs and other semiconductor alloys can be used to build up heterostructures that operate at other terahertz frequencies. See R. Kohler et al., "Terahertz semiconductor-heterostructure laser," *Nature* 417, 156 (2002), which is incorporated herein by reference.

The top and bottom waveguide layers 28 and 29 are typically metal or doped-semiconductor layers that keep the mode in the laser cavity. In the example shown in FIG. 2, both of the waveguide layers 28 and 29 are metallic. In particular, with terahertz QCLs the mode is confined by interaction with a surface plasmon at the semiconductor/metal interface. The waveguide layers can also provide electrical contacts to the semiconductor core 23. In the embodiment shown here, the Schottky diode 27 can be the small interface between the semiconductor core 23 and a metal post 24 connected to an antenna 26. To make a diode, the metal 25 at this interface must be rectifying. For example, titanium makes a particularly stable Schottky contact to a GaAs-based semiconductor core. The electrical contact and waveguide layers 28 and 29 over the rest of the semiconductor core 23 can be a different metal that preferably provides an ohmic contact to the semiconductor material, rather than a rectifying contact. Typically, a combination of metals can be used to make the ohmic contact. For example, metal stacks of nickel, gold, and germanium, or palladium, germanium, and gold, can be used to make ohmic contacts to GaAs-based semiconductor materials. The waveguide thicknesses can be one-micron or less, although a thicker bottom layer can be used to bond the laser to another metal for heat sinking.

TABLE 1

QCL GaAs/AlGaAs semiconductor core

| material | doping | thickness (Å) | |
|---|---|---|---|
| GaAs | LTG cap layer | 35.0 | |
| GaAs | $5 \times 10^{19}$ cm$^{-3}$ | 100.0 | |
| GaAs | $5 \times 10^{18}$ cm$^{-3}$ | 500.0 | |
| Al$_{0.15}$Ga$_{0.85}$As | undoped | 42.6 | |
| GaAs | $1.9 \times 10^{16}$ cm$^{-3}$ | 160.8 | |
| Al$_{0.15}$Ga$_{0.85}$As | undoped | 36.3 | |
| GaAs | undoped | 94.4 | |
| Al$_{0.15}$Ga$_{0.85}$As | undoped | 47.4 | |
| GaAs | undoped | 82.2 | ↑ |
| Al$_{0.15}$Ga$_{0.85}$As | undoped | 27.9 | ↑ |
| GaAs | undoped | 68.1 | ↑ |
| Al$_{0.15}$Ga$_{0.85}$As | undoped | 42.6 | repeat |
| GaAs | $1.9 \times 10^{16}$ cm$^{-3}$ | 160.8 | 178 times |

TABLE 1-continued

QCL GaAs/AlGaAs semiconductor core

| material | doping | thickness (Å) | |
|---|---|---|---|
| $Al_{0.15}Ga_{0.85}As$ | undoped | 36.3 | ↓ |
| GaAs | undoped | 94.4 | ↓ |
| $Al_{0.15}Ga_{0.85}As$ | undoped | 47.4 | ↓ |
| GaAs | $3 \times 10^{18}$ cm$^{-3}$ | 7000.0 | |
| $Al_{0.55}Ga_{0.45}As$ | undoped | 2000.0 | |

Above the Schottky contact 27, many metals can be used in the post 24 and antenna 26, so long as they do not affect the Schottky contact. The antenna 26 preferably has a low surface resistance and is structurally rigid. For example, gold can be used to provide the desired antenna properties. A palladium-gold or platinum-gold alloy can cover the diode to prevent diffusion to the titanium contact. A variety of antenna or horn configurations can be used. In FIG. 2 is shown a patch antenna. For example, the patch antenna can be approximately 50 microns square and a couple microns in thickness.

When a electromagnetic field is coupled to the Schottky diode (the point contact), a change in the low frequency electrical response is observed due to the rectifying nature of the point contact. If the field amplitude remains constant in time this change will remain constant in time. If two fields are coupled to the mixer, the instantaneous field amplitude will be modulated in time. This modulation occurs at the difference, or intermediate frequency due to the superposition of the two fields. This IF signal can be measured, for example with a spectrum analyzer. If one of the fields that is created by the QCL is defined as the LO, the frequency of all other fields incident on the antenna can then be determined "simultaneously" by sweeping the spectrum analyzer.

In the typical approach to heterodyne detection, the LO is provided by a separate source and both it and the incident radiation of interest are coupled to the mixer by focusing them onto the mixer. As shown in FIG. 2, with the integrated heterodyne transceiver 20 of the present invention, the incident radiation 15 is likewise focused onto an antenna 26 which couples it to the mixer 27. The LO power, however, is coupled directly to the mixer 27, due to the intrinsic properties of a terahertz QCL 22.

Figure 3A:
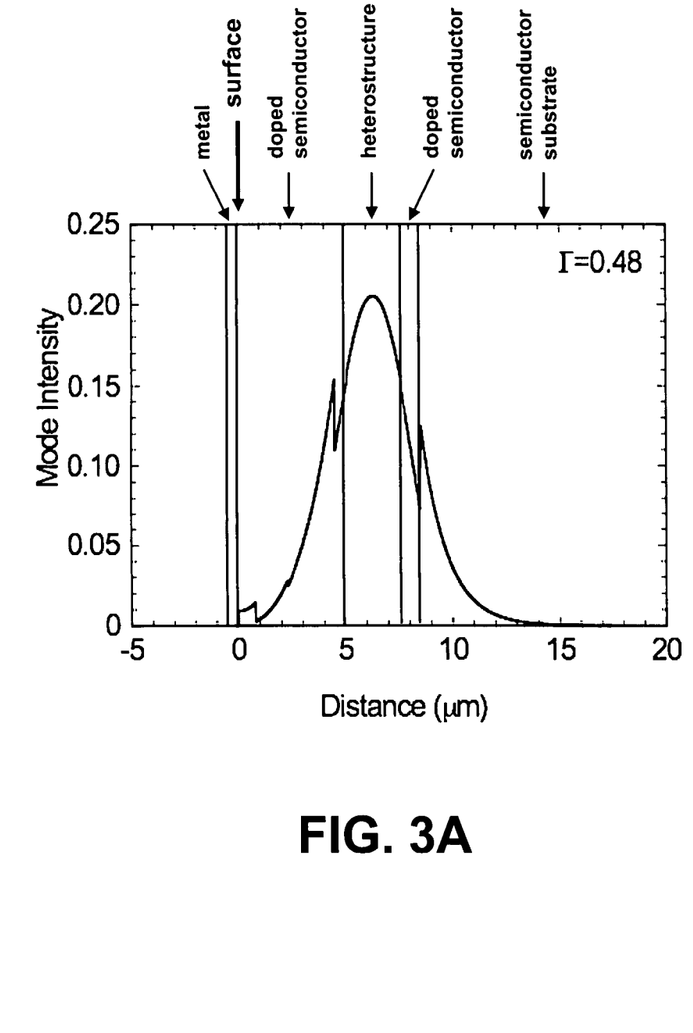
FIG. 3A shows the spatial dependence of the laser field intensity inside the laser cavity for a standard shorter wavelength semiconductor laser.
Figure 3B:
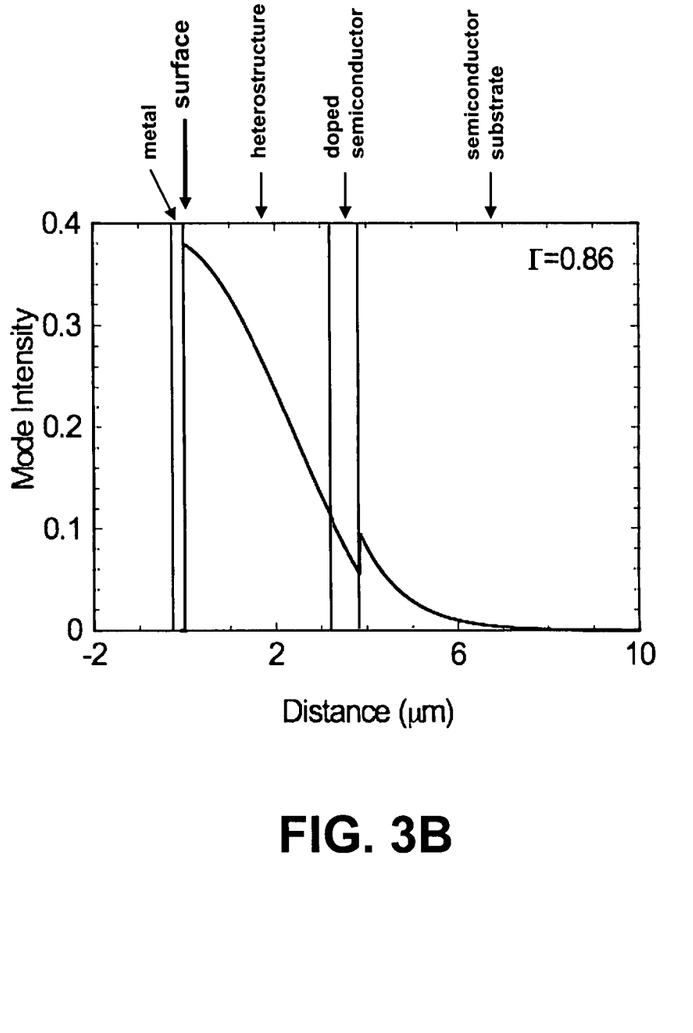
FIG. 3B shows the spatial dependence of the laser field intensity inside the laser cavity for a terahertz QCL comprising a metal/semiconductor waveguide.

In FIGS. 3A and 3B are shown the spatial dependences of the laser field intensity inside the laser cavity formed by the active semiconductor core, for standard shorter wavelength semiconductor lasers and a terahertz QCL, respectively. In these figures, the metal-waveguide-layer/semiconductor interface is on the left. As shown in FIG. 3A, the field intensity near the surface is very weak for the standard semiconductor laser. However, as shown in FIG. 3B, the field intensity of a terahertz QCL peaks at the surface and enables the integration of the QCL with the Schottky diode. Therefore, the field is high at the metal/semiconductor interface defining the Schottky diode and coupling of the LO from the terahertz QCL is achieved without the use of an antenna. See R. Sachs and H. G. Roskos, "Mode calculations for a terahertz quantum cascade laser," *Optics Express* 12, 2062 (2004); O. Demichel. et al., "Surface plasmon photonic structures in terahertz quantum cascade lasers," *Optics Express* 14, 5335 (2006); S. Kohen et al., "Electromagnetic modeling of terahertz quantum cascade laser waveguides," *J. Appl. Phys.* 97, 053106 (2005); and Q. Hu et al., "Resonant-phonon-assisted THz quantum-cascade lasers with metal-metal waveguides," *Semicond. Sci. Technol.* 20, S228 (2005), which are incorporated herein by reference.

Figure 4A:
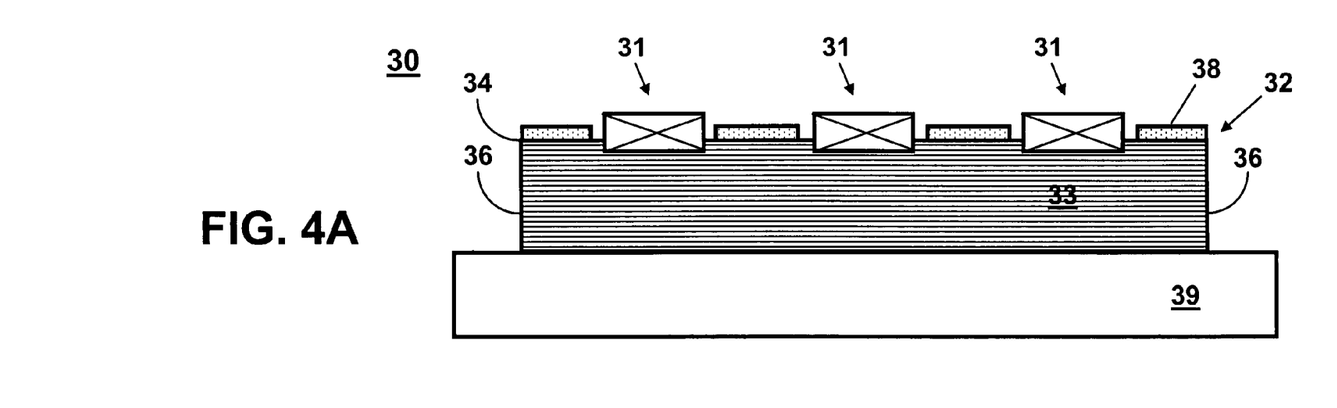
FIG. 4A shows a side-view schematic illustration of an integrated heterodyne terahertz transceiver comprising an array of receivers.
Figure 4B:
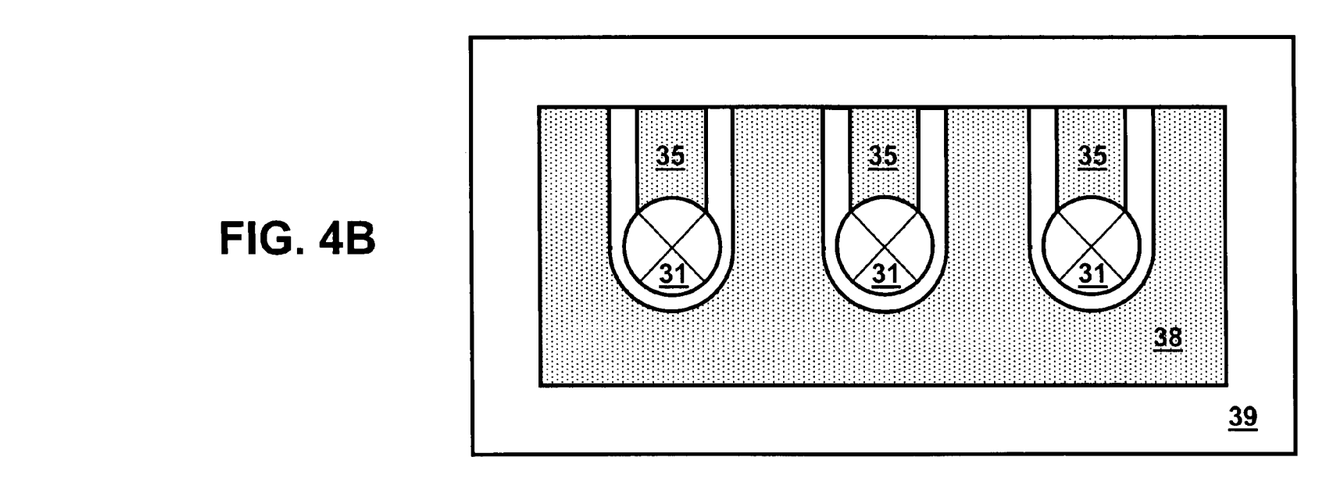

In FIG. 4A is shown a side-view schematic illustration of another embodiment 30 of the integrated heterodyne terahertz transceiver 10 comprising an array of three separate receivers 31 on top of a semiconductor core ridge structure 33. The ridge structure 33 provides the laser cavity of the QCL 32. A typical ridge structure is 30- to 400-μm wide and one- to a few-millimeters long. The ridge structure 33 can be formed on a substrate 39 that provides the bottom electrical contact and bottom waveguide layer. For example, a GaAs-based heterostructure can be built on a GaAs substrate. Alternatively, the QCL can be bonded to a metal layer on a GaAs substrate, or directly to a metal that has the same thermal expansion coefficient as the semiconductor core material (e.g., tungsten-copper for a GaAs-based core). An array of holes is formed through the QCL's top electrical contact and waveguide metallization 38 to expose the underlying semiconductor. Each receiver 31 comprises a separate antenna 26 and mixer 27, similar to those shown in FIG. 2. Each receiver 31 can be monolithically fabricated or flip-chip bonded to the exposed top surface of the ridge structure 33 to form the metal-to-semiconductor contact of the Schottky diode mixer. The size of the diode mixer and the hole will depend on the frequency of the laser, but can typically be about one-tenth micron and a couple microns, respectively. The spatial strength of the field inside the laser cavity peaks at the top surface 34 of the ridge structure 33. The mixer portion of the receiver 31 can be flush with or protrude into the propagating terahertz field inside the ridge structure 33, so that a small fraction of the internal terahertz field can be drawn off to supply the LO power to the mixer. Since the difference IF signal can be any frequency up to the bandwidth of the mixer (e.g., DC to 40 GHz or higher), high-frequency leads are required to bring the IF signal off the chip. As shown in FIG. 4B, this high-frequency lead 35 can comprise a coplanar waveguide (as shown) for each receiver 31. For example, the coplanar waveguide can comprise gold. Alternatively, other types of high-frequency leads, such as a microstrip line or high-frequency waveguide can be fabricated lithographically on top surface of the QCL ridge cavity.

When operated in an active mode, the transceiver's target illumination signal can be broadcast from an end facet 36 of the QCL cavity 33. Typically, the end facet 36 can be the cleaved end of the QCL bar. With plasmon waveguided laser cavities, the reflectivity of a cleaved end facet is about 30%. With a metal-metal waveguide, the reflectivity can be higher, for example, 85%. The return signal from the target is received by the antenna connected to the metal anode of the mixer diode of each receiver 31. Alternatively, if the target passively radiates its own light and the transceiver 30 is only needed to operate as a heterodyne receiver, high-reflectivity facets can be formed on the end facets of the laser, further increasing the device efficiency and maximum operation temperature. For example, the reflectivity of the end facets can be increased by applying an insulator to a cleaved end facet and covering them with a gold layer. In either the active or passive mode, supplying the LO power to the mixer in this integrated method differs from the conventional method of simply shining light from a QCL's facet output onto the mixer, either through a free-space or an on-chip waveguide. Because this internal terahertz field is larger than the terahertz field exiting the output facet of the laser, this integrated method of delivering LO power to the mixer has advantages in power efficiency, compactness, simplicity, and flexibility of design over conventional methods of supplying LO power to the mixer.

Finally, because the mixer is embedded in the laser semiconductor core, the transceiver can be used as an internal diagnostic to monitor the QCL performance itself. For example, the mixer can act as a power meter when the laser is running single mode, and will indicate a heterodyne beat signal if the laser starts running multi-mode. Since single-mode operation is important for many of the above applications, being able to confirm that the laser is running single mode is a great advantage.

The present invention has been described as an integrated heterodyne terahertz transceiver. It will be understood that the above description is merely illustrative of the applications of the principles of the present invention, the scope of which is to be determined by the claims viewed in light of the specification. Other variants and modifications of the invention will be apparent to those of skill in the art.

We claim:

1. An integrated heterodyne terahertz transceiver, comprising:
    a quantum cascade laser, comprising
        a substrate providing a bottom waveguide layer,
        a plurality of layered heterostructures of two or more semiconductor alloys on the substrate,
        a top waveguide layer on the layered semiconductor heterostructures, thereby providing an active semiconductor core between the top and bottom waveguide layers; and
    at least one receiver formed in a hole in the top waveguide layer of the quantum cascade laser, comprising
        a rectifying metal contact on the top surface of the layered semiconductor heterostructures exposed by the hole, thereby forming a metal-to-semiconductor Schottky diode, and
        an antenna or horn connected to the rectifying metal contact for receiving a terahertz signal;
    wherein the quantum cascade laser couples terahertz local oscillator power to the Schottky diode to mix with the received terahertz signal to provide an intermediate frequency output signal.

2. The integrated heterodyne terahertz transceiver of claim 1, wherein the substrate comprises a semiconductor or metal.

3. The integrated heterodyne terahertz transceiver of claim 2, wherein the semiconductor substrate comprises gallium arsenide.

4. The integrated heterodyne terahertz transceiver of claim 1, wherein the layered semiconductor heterostructures comprise a ridge structure.

5. The integrated heterodyne terahertz transceiver of claim 1, wherein the two or more semiconductor alloys comprise gallium arsenide and aluminum gallium arsenide.

6. The integrated heterodyne terahertz transceiver of claim 1, wherein the top waveguide layer comprises a metal or a doped semiconductor.

7. The integrated heterodyne terahertz transceiver of claim 6, wherein the metal comprises gold.

8. The integrated heterodyne terahertz transceiver of claim 6, wherein the metal comprises a metal stack of nickel, gold, and germanium, or palladium, germanium, and gold.

9. The integrated heterodyne terahertz transceiver of claim 1, wherein the bottom waveguide layer comprises a metal or a doped semiconductor.

10. The integrated heterodyne terahertz transceiver of claim 9, wherein the metal comprises gold.

11. The integrated heterodyne terahertz transceiver of claim 9, wherein the metal comprises a metal stack of nickel, gold, and germanium, or palladium, germanium, and gold.

12. The integrated heterodyne terahertz transceiver of claim 1, wherein the rectifying metal contact comprises titanium.

13. The integrated heterodyne terahertz transceiver of claim 1, wherein the antenna comprises a patch antenna.

14. The integrated heterodyne terahertz transceiver of claim 1, wherein the received terahertz signal has a frequency of 100 GHz to 10 THz.

15. The integrated heterodyne terahertz transceiver of claim 1, further comprising a coplanar waveguide or microstrip line on the layered semiconductor heterostructures to bring off the intermediate frequency output signal.

* * * * *